United States Patent [19]

Gonser

[11] Patent Number: 5,779,474
[45] Date of Patent: Jul. 14, 1998

[54] SUDDEN STOP MECHANISM AND AIR-GAP SEAL FOR DENTAL HANDPIECE

[75] Inventor: Donald L Gonser, Lanscaster, Pa.

[73] Assignee: Den-Tal-Ez, Inc., Conshohocken, Pa.

[21] Appl. No.: 770,485

[22] Filed: Dec. 20, 1996

Related U.S. Application Data

[63] Continuation of Ser. No. 257,209, Jun. 9, 1994, abandoned.

[51] Int. Cl.⁶ .................. A61C 1/05; A61C 1/14
[52] U.S. Cl. .................. 433/129; 433/106; 433/132
[58] Field of Search .................. 433/98, 99, 104, 433/106, 114, 115, 126–129, 132; 415/123, 904

[56] References Cited

U.S. PATENT DOCUMENTS

| | | | |
|---|---|---|---|
| 2,791,835 | 5/1957 | Staunt | 433/128 |
| 2,895,738 | 7/1959 | Baker | 279/53 |
| 3,082,528 | 3/1963 | Reid | 433/127 |
| 3,132,426 | 5/1964 | White | 415/123 |
| 3,324,552 | 6/1967 | Saffir | 433/82 |
| 3,712,386 | 1/1973 | Peters | 415/904 |
| 3,798,775 | 3/1974 | Weinberg et al. | 433/85 |
| 4,012,841 | 3/1977 | Mosimann | 433/127 |
| 4,021,918 | 5/1977 | Bailey | 433/127 |
| 4,292,027 | 9/1981 | Richmond | 433/115 |
| 4,295,830 | 10/1981 | Uchida | 433/115 |
| 4,318,695 | 3/1982 | Lieb et al. | 433/132 |
| 4,369,034 | 1/1983 | Garnier et al. | 433/115 |
| 4,470,813 | 9/1984 | Thorburn | 433/132 |
| 4,595,363 | 6/1986 | Nakanishi | 433/129 |
| 4,773,856 | 9/1988 | Mosimann | 433/127 |
| 4,797,098 | 1/1989 | Kawata | 433/98 |
| 4,966,552 | 10/1990 | Gonser | 433/132 |
| 5,074,788 | 12/1991 | Nakanishi | 433/115 |
| 5,252,065 | 10/1993 | Nakanishi | 433/115 |
| 5,423,678 | 6/1995 | Nakanishi | 433/115 |

FOREIGN PATENT DOCUMENTS

| | | | |
|---|---|---|---|
| 497139 | 8/1992 | European Pat. Off. | 433/114 |
| 2905484 | 8/1979 | Germany | 433/127 |
| 998442 | 7/1965 | United Kingdom | 433/132 |

Primary Examiner—Stephen R. Funk
Attorney, Agent, or Firm—Panitch Schwarze Jacobs & Nadel, P.C.

[57] ABSTRACT

A high speed air-driven powerhead in a dental handpiece includes an automatic chuck with outside surfaces protection from overheating. An autochuck release push button on the back of the powerhead is constructed of low thermal conductivity and heat reflective materials to reduce heat due to friction from inadvertent contact with the chuck while rotating. In addition, a sudden stop mechanism is provided which arrests chuck rotation if the force of contact exceeds a level which would raise the temperature of the push button beyond a predetermined threshold. A vortex air barrier is also provided to seal the front end bearing of the powerhead. The barrier also permits spacing which prevents static axial overload of the bearing and eliminates possible damage to the bearing.

55 Claims, 4 Drawing Sheets

SUDDEN STOP MECHANISM AND AIR-GAP SEAL FOR DENTAL HANDPIECE

This application is a continuation of application Ser. No. 08/257,209 filed on Jun. 9, 1994, now abandoned.

FIELD OF THE INVENTION

The present invention relates generally to dental handpieces, and more particularly to a sudden stop mechanism and air-gap seal for an air-driven automatic chuck in a dental handpiece.

BACKGROUND OF THE INVENTION

An air-driven automatic chuck, also referred to as an autochuck, in a powerhead of a dental handpiece typically includes a spring which applies an axial force to radially adjustable jaws within a spindle to close and frictionally hold the shank of a tool. An opposite force applied by a finger-operated release push button on the back of the powerhead opens the jaws for permitting a tool to be inserted or removed. A dental handpiece generally describing this arrangement is disclosed in U.S. Pat. No. 4,595,363.

One of many and complex problems encountered in high speed handpieces is overheating. Under normal conditions of use, there is a slight gap between the rotating chuck and the release push button in order to prevent friction contact and overheating. But if the push button is pressed while the chuck is rotating at a high speed of 100,000 to 500,000 rpm, friction contact may rapidly overheat the push button without warning. Any tissue touched by a hot push button may experience an undesirable sensation of heat. In extreme cases this could result in tissue burn to either the patient or the dentist.

Studies have indicated that human tissue can burn, and experience pain, if exposed for as little as fifteen seconds to heat above a threshold temperature of 45° C. (113° F.). If the release push button is designed with relatively light spring to allow an operator to manipulate it with ease, improper operator use, such as pressing the button while the turbine is still running at high speed, can cause operator discomfort. Also, as components in the powerhead wear, the gap between the chuck and push button may eventually close and produce the same result.

During operation, there is also drive air leakage through the shaft front end bearings of the powerhead. In prior designs as much as 30% of the drive air escapes in this manner without ever reaching the air exhaust ports. The escaping air blows out factory preloaded grease which causes the powerhead to heat up and shorten bearing life. As the bearings begin to fail, their increased friction generates even more heat to the point where the temperature of the entire housing and particularly the autochuck release push button as well becomes excessive and intolerable to the patient, or to the touch of the dentist. Similarly, when the drive air supply is shut off and the rotating parts coast to a stop, the vacuum created in the powerhead may suck debris such as tooth particles, almalgam, other restorative materials and saliva into its moving parts and obviously affect turbine operation to adversely reduce performance of the handpiece. Maintenance of sterility of the handpiece is also made more difficult and tenuous.

Various designs in the powerhead have been attempted to reduce overheating the powerhead and autochuck release push button. For instance, U.S. Pat. No. 4,773,856 and German Patent 2905484 each describe an automatic chuck which makes substantially point contact at the axis of relative rotation between the release push button and the chuck. So long as point contact is present there is relatively little friction, and a lower temperature rise to the push button than otherwise would be produced. However, the potential for a temperature rise high enough to burn, is still present. Over time the point contact will wear flat and the increased surface friction will produce more heat and raise the temperature to a much more undesirable level and increase the potential for tissue burn.

Modifications have also been proposed or implemented with the singular purpose of preventing air leakage or debris infiltration at the gap between the housing and spindle. For instance U.S. Pat. Nos. 3,798,775 and 4,295,830 teach sealing rings along the shaft to prevent leakage; and U.S. Pat. Nos. 2,791,835 and 3,324,552 teach flanges mounted on the shaft for throwing off debris by centrifugal force through an exit port provided in the turbine housing.

SUMMARY OF THE INVENTION

Accordingly, it is an object of the present invention to provide a heat sterilizable air-driven powerhead in a dental handpiece with protection against bearing overload and bearing damage, overheating, air leakage, and debris infiltration.

Another object of the invention is to provide in a high speed dental handpiece having an automatic chuck, thermal protection from heat generated upon brief frictional contact of the chuck and the tool release push button.

A further object of the invention is to provide, in a dental handpiece, a push button operated automatic chuck which reduces risk of injury due to transfer of heat of friction if the push button is inadvertently pressed while the chuck is rotating.

A still further object of the invention is to provide, in a dental handpiece, a push button operated automatic chuck which will immediately arrest rotation if a frictional force between the chuck and the push button is exceeded.

Another object of the invention is to provide a multiple function sudden stop mechanism and air-gap seal in an air-driven powerhead of a dental handpiece to prevent escape of drive air, debris infiltration, loss of factory preload grease, and bearing load limiting.

Still another object of the invention is to provide a novel and improved powerhead for a dental handpiece with substantially no increase in overall dimensions, which is durable, sterilizable and relatively simple in design and construction, and which can be economically manufactured.

Still another object of the invention is to provide a novel and improved powerhead with a rotating shaft spacer stop for preventing overload of the autochuck bearing or bearings.

Briefly, these and other objects of the present invention are achieved in an air-driven powerhead of a dental handpiece having a rotary automatic chuck which is axially moveable in front and rear end bearings between tool holding and releasing positions by forces applied by an operator through a spring-loaded release push button. Transfer of heat generated by inadvertent friction contact of the push button with the chuck, while the chuck is rotating at high speed, is reduced by the combined use in the push button of materials having a very low coefficient of thermal conductivity and high reflectivity and a sudden stop mechanism.

The sudden stop mechanism is interconnected between the housing of the handpiece and the chuck for arresting rotation if the friction force between the chuck and the push button exceeds a level which would raise the temperature of the push button above a predetermined threshold. In one embodiment, the chuck is suddenly stopped when radial arms, rotating with the chuck, shift axially and strike stationary pins in the powerhead housing. In another embodiment, the chuck is suddenly stopped when an annular stepped collar rotating with the chuck axially shifts and frictionally engages the front end of the housing. In addition, the rotating collar forms vortexes which sets up eddy currents of air at its periphery creating an air barrier or curtain in which the eddy currents rotate at 90 degrees to the normal air flow direction in the annular gap between the rotating collar and the stationary housing. This prevents drive air from escaping and blowing out factory preloaded grease which is one cause of overheating. It also serves as a seal against debris infiltration and loss of turbine power. The air seal forces normal air flow through the turbine to the exhaust port thereby maximizing the self-cooling properties of the powerhead.

The annular stepped collar mounted on the rotating shaft also serves as a spacer which limits the load that can be placed on the front bearing, for example four pounds, when the autochuck release push button is pressed to release the tool. The bearing design will be damaged when the axial load exceeds the design limit, such as four pounds for ceramic balls and ten pounds for steel balls.

BRIEF DESCRIPTION OF THE DRAWINGS

The foregoing and other objects, features and advantages of the invention will become apparent from the following description, when taken in conjunction with the accompanying drawings wherein.

DESCRIPTION OF THE PREFERRED EMBODIMENTS

Figure 1:
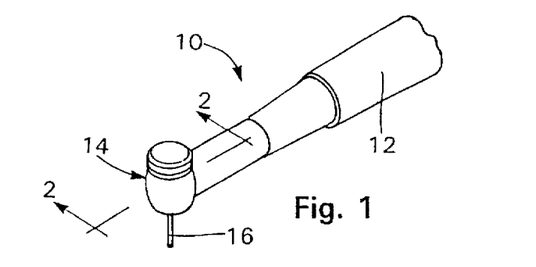
FIG. 1 is a perspective view of a powerhead on the distal end of a dental handpiece, the powerhead including an automatic chuck with thermal protection according to the present invention.

Referring now to the drawings wherein like characters represent like or corresponding parts throughout the several views, there is shown in FIG. 1 the distal end of a high-speed dental handpiece 10 with thermal protection according to the invention. It includes a handle 12 with a fiber optics light tube 13 (FIG. 2) and a powerhead 14 in which a burr 16 or similar tool is inserted for rotation on an axis generally perpendicular to the length of handle 12. The physical size of powerhead 14 is critical for use in the oral cavity, particularly when used on the buccal surfaces of posterior teeth and for best high speed performance. In the preferred embodiments, the maximum height of the head is approximately 13 mm to 14 mm.

Figures 2, 3, 8:
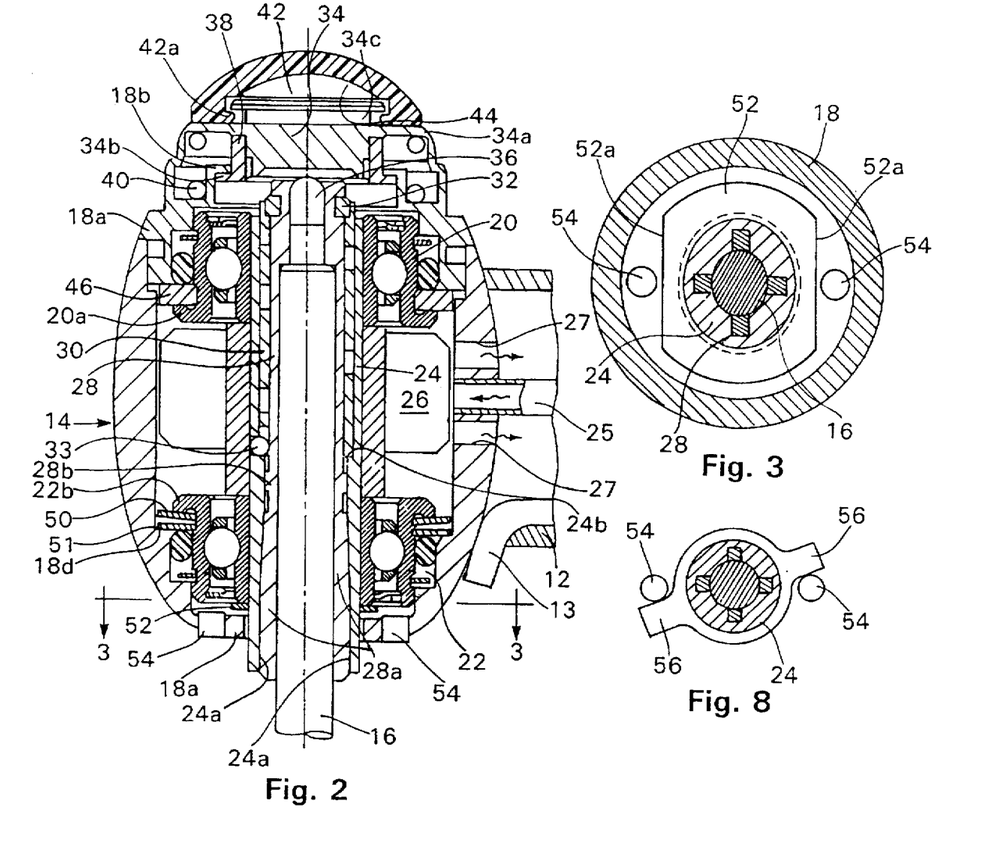
FIG. 2 is an enlarged cross-sectional view of the powerhead taken along the line 2—2 of FIG. 1 showing the automatic chuck in a normal operating position.
FIG. 3 is a cross-sectional view of the powerhead taken in a transverse plane along the line 3—3 of FIG. 2 with a sudden stop mechanism according to one embodiment of the invention in a non-arresting position.
FIG. 8 shows a sudden stop mechanism according to another embodiment of the invention in a non-arresting position.

As shown in more detail in FIG. 2, powerhead 14 includes a hollow cylindrical housing 18, a top cover 18a, and coaxial rear and front anti-friction ball bearings 20 and 22 rotatably supporting a hollow spindle 24 in housing 18. An inlet port 25 provides drive air for rotating a turbine of radial blades 26 fixed around spindle 24 between bearings 20 and 22, and exhaust ports 27 discharge the spent air through handle 12. A hollow collet 28 axially slidable within spindle 24 has equally spaced radial jaws 28a at the lower end which taper outwardly to slide in complementary tapered radial slots 24a in spindle 24. A first coil spring 30 wound lengthwise between spindle 24 and collet 28 is seated in compression between a shoulder 24b of spindle 24 and a retainer 32 fixed in a groove around the rearward end of collet 28. The compression force of spring 30 urges collet 28 rearward into spindle 24 forcing jaws 28a to deflect radially inward and grip the shank of burr 16. The rearward travel of collet 28 is limited by a ball 33 captured in a socket of spindle 24 and engaged by a shoulder 28b. In an actual embodiment, a tool pullout force of 3.3 pounds minimum due to compression force is applied at the rearward limit of collet 28.

Burr 16 may be released by moving collet 28 forward in opposition to the force of spring 30 to relax jaws 28a. This is accomplished by a circular pusher plate 34 threaded into an annular retainer 38 which, in turn, slides in a circular lip 18b of top cover 18a. Plate 34 has an interior surface 34d which is positioned to press against the convex surface of a dome pin 36 fixed to and projecting from the upper end of collet 28. Its point of contact with pin 36 coincides with the axis of rotation of spindle 24 to minimize friction under relative rotation. Also, dome pin 36 serves to plug the through-hole where debris can originate from the rotating burr 16.

A second coil spring 40 seated in compression between facing surfaces of cover 18a and an annular flange 34a of plate 34 normally maintains a gap in the order of 0.015 inch between plate 34 and the tip of dome pin 36. The rearward travel of plate 34 is stopped by an annular flange 34b engaging a lip 18b around the inside of cover 18a. In an actual embodiment, the spring imparts a compression force of 20 ounces at the rearward limit of plate 34. For resistance to wear, particularly at the point where they contact, plate 34 and dome 36 are preferably a hardened steel such as martensitic stainless steel AISI Type 416 or 431.

An insulator-type end cap 42 constructed from materials, such as injection moldable polytetrafluoroethylene (PTFE) polymers including TEFLON® FEP or PFA, having a low thermal conductivity in the order of 1.4±0.3 Btu.in/h.ft$^2$.°F., with the push plate 34 forms a push button for the operator to apply a release force to the automatic chuck. The interior of the cap is concave and spherical in shape for best optical reflection with an annular lip 42a on the rim which snap-fits into a groove 34c in the rearward side of plate 34 and forms an insulating air space A between the plate 34 and cap 42. The air space A and the very low thermal conductivity of end cap 42 together significantly reduce transfer to the exposed side of cap 42 of any heat generated by friction at the point contact of plate 34 and dome pin 36. In addition, the interior arcuate surface of cap 42 is faced with a infrared reflective laminate 44, such as gold plating, to reflect back toward the plate 34 heat radiated therefrom. White PTFE polymers provide reflectivity greater than 50% and have been satisfactory in actual application experiments. The insulator-type end cap 42 could also be constructed from low thermal conduction ceramics or gold plated thermal conduction ceramics.

The above-described features as implemented in the automatic chuck significantly lessen the threat of exceeding the undesirable threshold temperature but under extreme conditions of friction contact, these precautions may not in and of themselves be sufficient. Therefore, the invention further provides for suddenly arresting rotation of the chuck by permitting bearings 20 and 22 to shift within housing 18 between upper and lower axial limits by mounting the turbine on soft compressible O-rings. The bearings are normally urged toward the rearward limit by a wavy third annular spring 50 mounted between a flange 22b around the outer race of bearing 22 and a washer 51 resting against an adjacent shoulder 18d on the interior surface of housing 18.

In an actual embodiment, the spring rate of spring 50 is 50 pounds per inch and imparts a compression force of 1.075 ounces at the rearward limit of bearings 20 and 22. The rearward limit is determined by a ring 46, fixed to the interior surface of housing 18, acting against a flange 20a on the outer race of bearing 20; and the forward limit is determined by a disk brake 52 striking against a pair of radially opposite pins 54 protruding into the housing cavity from a bottom wall 18e of housing 18.

Figure 4:
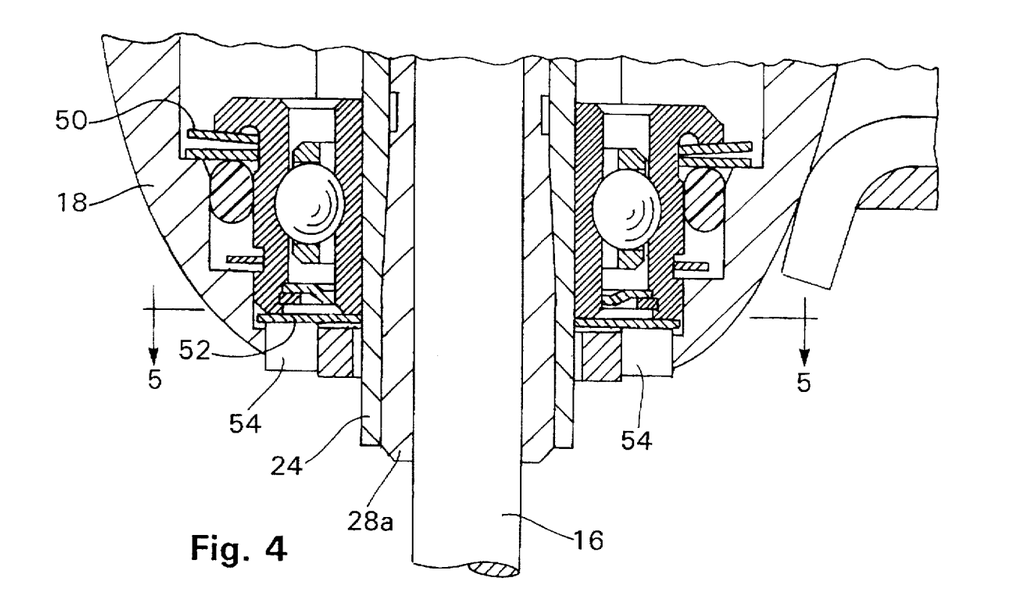
FIG. 4 is an enlarged view of the lower portion of FIG. 2 but with the sudden stop mechanism in a non-arresting position but in frictional contact.
Figure 5:
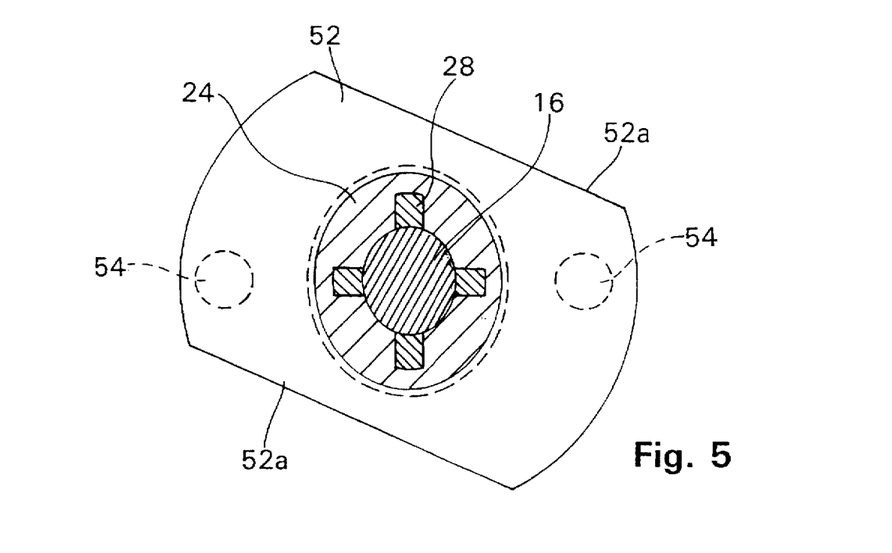
FIG. 5 shows the sudden stop mechanism of FIG. 4 as viewed along the line 5—5.
Figure 6:
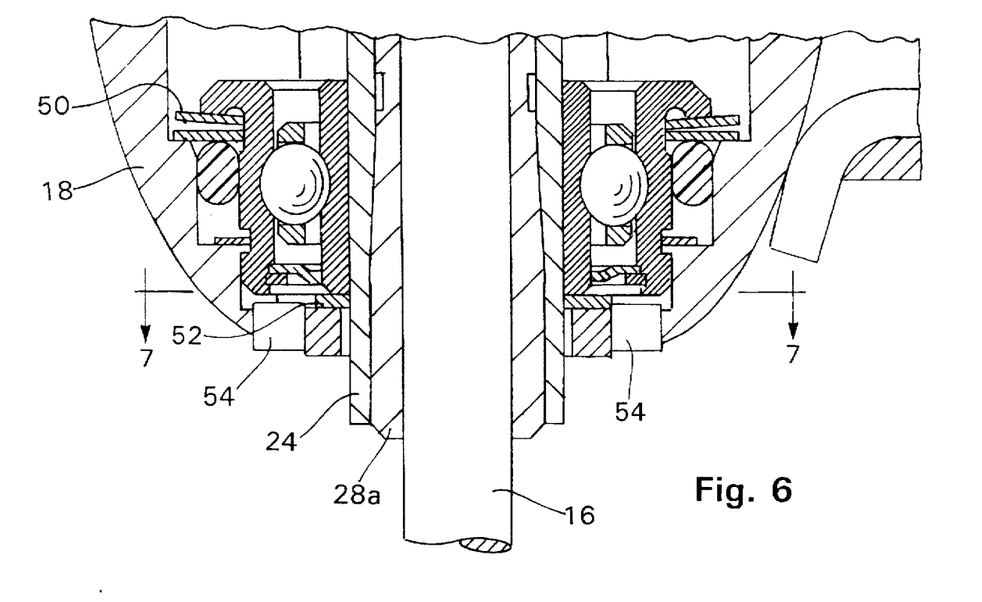
FIG. 6 is an enlarged view of the lower portion of FIG. 2 but with the sudden stop mechanism in an arresting position.
Figure 7:
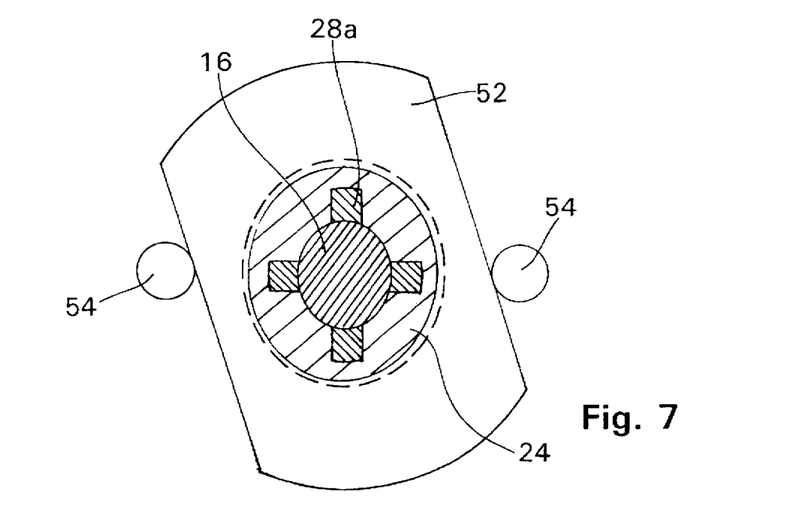
FIG. 7 shows the sudden stop mechanism of FIG. 6 as viewed along the line 7—7.

Brake 52, consisting essentially of an oblong disk, having a pair of opposing flats or lands 52a is fixed to the outer surface of spindle 24. At the rearward limit of bearings 20 and 22, the axial clearance between brake 52 and pins 54 permits rotation of the chuck. However, in the position illustrated in FIGS. 4 and 5, a force applied to end cap 42, slightly exceeding the combined resistance of springs 30, 40 and 50 applied to dome pin 36, causes brake 52 to just slide across the facing ends of pins 54. The amount of heat generated at the point contact of plate 34 and dome pin 36 under this force may produce a slight, inconsequential warming of end cap 42. However, a rapid increase above an undesirable threshold temperature of 45° C., such as may occur with a higher force, is prevented by brake 52 shifting farther and striking the sides of abutment pins 54, as shown in FIGS. 6 and 7, to suddenly arrest chuck rotation.

FIG. 8 illustrates another embodiment of the disk brake in which radial arms 56 rotate with spindle 24 and strike pins 54 to stop chuck rotation when the downward force applied to end cap 42 causes spindle 24 to shift forwardly.

In the arresting position of brake 52 or arms 56, the external force applied to end cap 42 must exceed the combined resistance of springs 30, 40 and 50 applied to dome pin 36. A further increase in the external force begins to move collet 28 forward to open jaws 28a. The combined resistance of the springs should be as low as possible in order to enable a light touch of the fingers, in the order of 112 ounces, to open collet jaws 28a.

Figure 9:
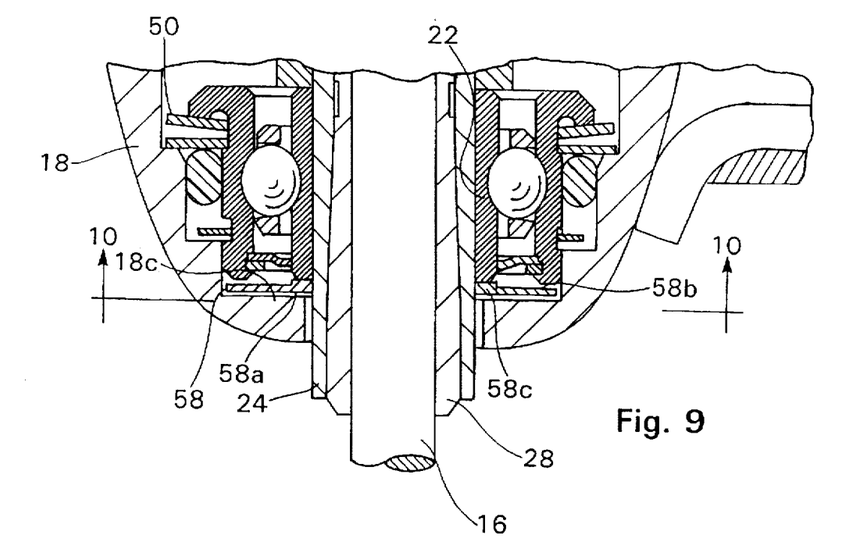
FIG. 9 is an enlarged view in cross-section of a front portion of the powerhead of FIG. 2 but with still another embodiment according to the invention of a sudden stop mechanism in a non-arresting position and also illustrating an air-gas seal.
Figure 10:
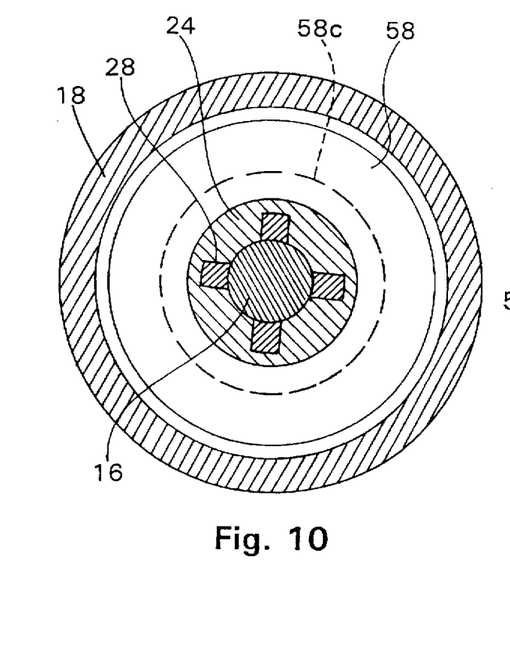
FIG. 10 is a cross-sectional view of the sudden stop mechanism of FIG. 9 as viewed along the line 10—10.

FIGS. 9 and 10 illustrate another embodiment of the sudden stop mechanism. A stepped disk brake 58, fixed around spindle 24, includes opposite sides 58a and 58b in axial clearance, respectively, of a facing annular shoulder 18c in the housing 18 and the outer race 22a of front bearing 22. The radial outer edge 58d of the disc 58 faces a solid wall 18d which extends upwardly from the shoulder 18c. The outer race 22a of the front bearing 22 contacts the wall 18d above the disk 58. A chamber 60 is formed by a nonforaminous outer wall defined by the shoulder 18c and the wall 18d. The nonforaminous outer wall can also include the outer race 22a of the bearing 22. The disc 58 is located within the chamber 60. The first side 58a, the radial outer edge 58d and a portion of the second side 58b of the disc 58 form an inner boundary for air in the chamber 60. The chamber 60 has two openings located on opposite sides of the disc 58. The first opening is located between the inner and outer races of the bearing 22, and the second opening is the axial opening in the housing through which the collet 24 passes. When a force is applied to end cap 42, the surface of moving brake 58 and stationary shoulder 18c frictionally engage, but raised portion 58c maintains sufficient clearance to prevent the force from being transmitted from brake 58 to the outer race. The friction force of brake 58 upon contact with shoulder 18c will suddenly arrest rotation of the chuck.

Stepped disk brake 58 also limits the maximum static thrust load an operator can apply to front bearing 22. The space taken up by brake 58 and its position limits the maximum compression travel, typically less than 0.010 inch, before it bottoms out onto stationary shoulder 18c. Wavy annular spring 50, with a greater total compression travel, such as 0.0215 inch, cannot be completely compressed due to disk brake portion 58c first bottoming out on the stationary surface of shoulder 18c. The axial load is thereby removed from front bearing 22. In an actual embodiment, the static thrust load for bearing 22 with ceramic balls in stainless steel raceways is 10 pounds; and for stainless steel balls is 16 pounds. The bearing load limit with ceramic balls is determined as the point where there is no evidence of "brinelling" or indentations in the raceways, the ceramic ball being harder is unaffected. However, the bearing load with stainless steel balls is at that point where there is no evidence of brinelling of the raceways and no smile-like imprint distortions on the ball.

Figure 9A:
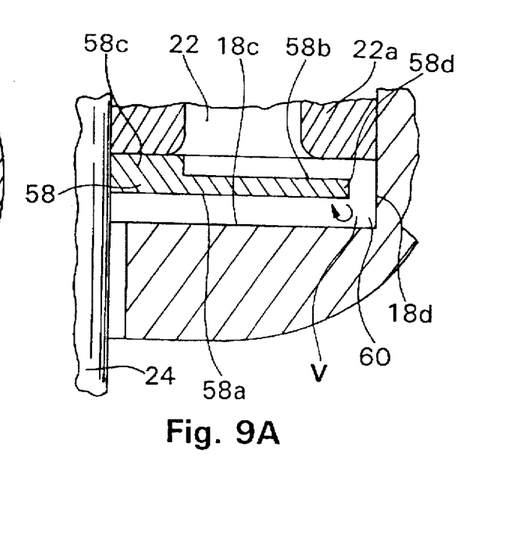
FIG. 9A is a greatly enlarged fragmentary cross-sectional view of a portion of the handpiece illustrated in FIG. 9 but showing the location of an air seal vortex formed during operation of the handpiece.

At normal operation speeds of the powerhead, the clearance of brake 58 between the outer race 22a of bearing 22 and shoulder 18c induces an annular vortex of air at the brake periphery which acts as an air barrier or curtain. During normal operation, escape of drive air from the powerhead is blocked by the air curtain thereby reserving the drive air for cooling powerhead 14 and push button 42. When the supply of drive air is shut off, the air curtain prevents debris from being drawn into the powerhead by the vacuum created during coasting of the rotating parts. The clearance required to produce the vortex air curtain v is a function of the drive air pressure, operating speed, flange size and properties of the facing surfaces. In general, the clearance should be less than about 0.010 inches, and preferably about 0.002 inches for operating speeds between 100,000 and 500,000 rpm. While the air seal is disclosed in combination with an autochuck-type handpiece, it can also be utilized in conventional non-autochuck handpieces as well.

Some of the many advantages and novel features of the invention should now be readily apparent. For example, thermal protection for a dental handpiece having an automatic chuck is provided whereby heat generated due to an inadvertent friction force between relative rotation of components will not overheat the release push button. Should the friction force exceed a predetermined level, rotation of the chuck is suddenly arrested. Means are also provided for preserving drive air for cooling by preventing leakage of the air from the powerhead, for preventing loss of factory-preloaded grease under positive air pressure conditions and infiltration of debris under vacuum operating conditions, and for limiting front bearing static thrust to safe non-damaging loads. These and other features as described are made possible by a unique design which requires substantially no increase in overall dimensions, produces a durable, sterilizable construction, and which can be economically manufactured.

It will be understood, of course, that various changes in the details, materials, steps and arrangement of parts, which have been herein described and illustrated in order to explain the nature of the invention, may be made by those skilled in the art within the principle and scope of the invention as expressed in the appended claims.

I claim:

1. In a dental handpiece having an autochuck with a collet rotatable in a housing for releasably mounting a tool, and a push button with a finger engageable surface, the push button being mounted for axial movement to actuate the collet, the improvement comprising:

means rotatable with the collet in closely spaced relation within said housing and operable in response to a predetermined axial movement of the push button to engage a stationary surface of the housing and completely arrest rotation of the collet without causing an undesirable level of heat to be sensed at the finger engageable surface.

2. A dental handpiece according to claim 1 wherein said rotatable means includes a braking surface extending radially of said collet for engagement with a confronting surface in said housing.

3. A dental handpiece according to claim 1 where said rotatable means includes at least a pair of arms extending radially outward of said collet and at least one abutment pin confronting said arms and engageable by one of said arms to effect said arrest of rotation of said collet.

4. A dental handpiece according to claim 1 wherein said push button has an interior surface confronting said collet, and said collet has a rotatable surface and means providing a substantially point contact surface normally disposed in spaced confronting relation with said push button interior surface and engageable therewith in response to displacement of said push button before said predetermined axial movement of said collet causes said rotatable means to engage said stationary surface and arrest rotation of the collet.

5. A dental handpiece according to claim 4 wherein said push button includes heat insulation between its finger engageable surface and its interior surface.

6. A dental handpiece according to claim 5 wherein said heat insulation includes a cap with a concave reflective surface adjacent said finger engageable surface for providing an air-gap within said push button and for reflecting heat back toward said collet, said cap being fabricated of a low-thermal conductivity material.

7. A dental handpiece according to claim 1 wherein said housing has an annular recessed surface surrounding an aperture rotatably receiving the collet, and said rotatable means on said collet includes a disc extending outwardly therefrom across said aperture in closely spaced relation with said recessed surface for providing an air seal during rotation of the collet to minimize positive pressure air loss and to prevent ingress of unwanted material into the handpiece during power off run-down when a vacuum is generated within the housing.

8. In a high-speed dental handpiece having a collet and an air-driven turbine mounted within a housing for rotating the collet extending through an aperture in the housing, the improvement comprising a recessed surface located around said aperture, a wall extending from said surface, and a radially extending disc mounted to said collet for rotation therewith in closely spaced relation with said surface, said surface and said wall forming a nonforaminous outer wall of a chamber in which the disc is located, rotation of the disc forms an active air seal in the chamber between the disc and the nonforaminous outer wall during rotation of the collet to minimize turbine air loss and to prevent ingress of unwanted material into the turbine during power-off run down of the turbine.

9. A high-speed handpiece according to claim 8 wherein said closely spaced relation is less than about 0.010 inches.

10. For use in a dental handpiece, an automatic chuck with thermal protection comprising, in combination:

a housing;
   a hollow spindle rotatably mounted on an axis in said housing;
   a collet having opposite ends and axially slidable in said spindle, one end forming a point of contact at said axis and the other end including jaws for gripping a tool;
   a first spring urging said collet rearward in said spindle;
   a pusher plate having opposite sides and axially movable in said housing, one side forming a surface transverse to said axis and facing the point of contact;
   a second spring urging said plate rearward to maintain a gap between said one side and the point of contact; and
   a thermal insulator secured to said plate forming with the other side of said plate an insulating air space.

11. An automatic chuck according to claim 10 further comprising:

a concave laminate secured to said insulator for reflecting back toward said plate heat radiated therefrom.

12. An automatic chuck according to claim 11 wherein:

the composition of said insulator consists essentially of a material selected from a group consisting of low thermal conduction ceramics and injection-moldable PTFE polymers.

13. An automatic chuck according to claim 11 wherein:

the composition of said laminate consists essentially of a material selected from a group consisting of gold plated thermal conduction ceramics and non-plated white injection-moldable PTFE polymers.

14. An automatic chuck according to claim 10 further comprising:

third spring means urging said spindle to a rearward position;
   brake means operatively connected between said spindle and said housing for arresting rotation of said spindle when the force applied to said plate axially moves said spindle forwardly against the combined forces of said first, second and third springs.

15. An automatic chuck according to claim 14 wherein:

said brake includes an annular disk; and
   said housing includes a surface axially spaced from and frictionally engaged by said disk when said spindle is in the forward position.

16. An automatic chuck according to claim 15 wherein:

the axial clearance between said disk and said surface is sufficient to provide vortexes at the periphery of said disk at a desired speed of rotation for creating a barrier to air flow.

17. An automatic chuck according to claim 10 further comprising said spindle being axially moveable in said housing;

a third spring urging said spindle to a rearward position;

brake means including a flange rotatable with said spindle and engageable with said housing when a forward force is applied to said plate in a predetermined amount exceeding the combined rearward forces of said first, second and third springs, said amount being sufficient to produce an undesirable rise in temperature in said insulator.

18. An automatic chuck according to claim 17 wherein said flange has radial arms extending from said spindle; and said housing includes projections axially spaced from said arms with said spindle in the rearward position.

19. An automatic chuck according to claim 10 further comprising:

means for allowing said spindle to move along said axis;

a third spring urging said spindle rearward;

an annular shoulder formed in the lower end of said housing around said spindle; and stop means fixed to said spindle for rotation therewith and including an annular washer normally positioned with axial clearance from said shoulder, and frictionally engageable with said shoulder when said plate applies a force to said collet exceeding the combined resistance force of said first, second and third springs an amount sufficient to produce an undesirable rise in temperature in said insulator.

20. Thermal protection in an automatic chuck, comprising, in combination:

a housing;

a hollow spindle with turbine blades rotatably mounted in said housing and axially slidable;

first spring means for urging said spindle rearward in said housing;

collet means axially slidable in said spindle for gripping a tool;

second spring means for urging said collet means rearward in said spindle;

pusher means movable axially in said housing for applying a force forwardly to said collet means;

third spring means for urging said pusher means rearwardly in spatial relation to said collet means; and brake means fixed to said spindle for arresting rotation of said spindle by a friction force applied to said collet means sufficient to produce an undesirable rise in temperature in said pusher means.

21. Thermal protection in an automatic chuck according to claim 20, wherein:

said first, second and third spring means have a combined compression force equal to the difference between the force applied to said pusher means and the force transmitted to said collet means.

22. Thermal protection in an automatic chuck according to claim 21 wherein:

said pusher means includes an insulation consisting essentially of a material selected from a group consisting of low thermal conduction ceramics and PTFE polymers.

23. Thermal protection in an automatic chuck according to claim 22 wherein:

said pusher means includes a concave interior surface forming an air space therein.

24. Thermal protection in an automatic chuck according to claim 23 wherein:

said concave surface comprises a heat reflective material.

25. Thermal protection in an automatic chuck according to claim 24 wherein:

said heat reflective material consists essentially of a material selected from a group consisting of reflective gold plating and white PTFE polymers.

26. Thermal protection for a dental handpiece having an automatic chuck, comprising, in combination:

a housing formed to be mounted on a distal end of the handpiece;

a hollow spindle with turbine blades rotatably mounted in said housing and slidable along an axis between forward and rearward positions of said housing;

a first spring normally urging said spindle toward the rearward position;

a collet axially slidable in said spindle with a rearward convex end forming a point contact at the axis of rotation, said collet including a tapered portion radially movable between forward and rearward positions in said spindle for respectively gripping and releasing the shank of a tool;

a second spring normally urging said collet toward the rearward position of said spindle;

a pusher plate movable axially in said housing between forward and rearward positions in said housing, said plate facing said convex end for moving said collet forwardly;

a third spring normally urging said plate rearward to form a gap with said convex end;

a thermally insulated end cap secured to an opposite surface of said plate, said cap having a concave interior surface forming an insulating air space with said plate;

brake means fixed for rotation with said spindle for arresting rotation when said spindle is moved forwardly along said axis to engage said housing; and said first, second and third springs have a combined compression force equal to the difference between a force applied to said end cap when said brake means is arrested, and a force required at the point of contact for generating a predetermined threshold temperature in said end cap.

27. Thermal protection in an automatic chuck according to claim 26, further comprising:

a projection in a forward wall of said housing adjacent to said spindle; and radial arms extending from said brake means for engaging said projection.

28. Thermal protection in an automatic chuck according to claim 26, further comprising:

a first friction surface in a forward wall of said housing adjacent to said spindle; and a second friction surface in said brake means for engaging said first friction surface.

29. Thermal protection in an automatic chuck according to claim 26, further comprising:

a reflective laminate secured to the concave interior surface of said thermally insulated end cap for reflecting heat radiated from said pusher plate.

30. For use in a dental handpiece, an automatic chuck with bearing thrust overload protection comprising, in combination:

a housing having forward and rearward ends;

a hollow spindle rotatably supported in said housing by inner and outer races respectively of coaxial forward and rearward bearings;

a collet axially slidable in said spindle, and having a forward end including jaws for gripping a tool and an opposing rearward end;

a first spring urging said collet rearward in said spindle;

a pusher plate having opposite sides and being positioned for axial movement in said housing, one side of the pusher plate facing the rearward end of the collet, the pusher plate further being positioned such that the one side presses said collet forwardly in said housing during at least part of the axial movement of the pusher plate;

a second spring urging said plate rearwardly to maintain a gap between said one side and the rearward end; and a third spring mounted on said outer race of said forward bearing and urging said forward bearing outer race rearwardly;

an annular shoulder formed in the forward end of said housing;

an annular disk fixed relative to said forward bearing inner race with an axial clearance facing said shoulder sufficient to limit the deflection of said third spring when a thrust load is applied to said pusher plate.

31. Apparatus according to claim 30 wherein the axial clearance is about 0.01 inch.

32. In a high speed dental handpiece having a collet and an air-driven turbine mounted within a housing for rotating the collet extending through an aperture in the housing, the housing including an internal surface surrounding said aperture, the improvement comprising a radially extending disc mounted to rotate with said collet, said disc being spaced a predetermined distance from said internal surface and a wall extending from said surface with the wall being offset from a radial outer edge of the disc, the internal surface and the wall defining a nonforaminous outer wall of a chamber in which the disc is located, said predetermined distance being selected to provide an active air seal between said disc and said nonforaminous outer wall during rotation of the collet to minimize turbine air loss and to prevent ingress of unwanted material into the turbine during power-off run down of the turbine.

33. A high speed handpiece according to claim 32 wherein said predetermined distance is less than about 0.010 inches.

34. A high speed dental handpiece according to claim 32 wherein said disc and internal surface extend generally parallel with respect to each other.

35. A high speed dental handpiece according to claim 32 wherein said active air seal is in the form of vortexes formed between said disc and internal surface during rotation of the collet.

36. A high speed dental handpiece as recited in claim 32, wherein said disc and internal surface extend generally perpendicularly from a longitudinal axis of said collet.

37. In a high speed dental handpiece having an assembly and a high speed, air-driven turbine mounted within a housing for rotating the assembly extending through an aperture in the housing at operating speeds of 100,000 RPM or more, the housing including a stationary internal surface surrounding said aperture, the improvement comprising disc means rotating with the assembly and overlapping the internal surface, and a wall extending from said surface and spaced radially from said disc means, the surface and the wall forming a nonforaminous outer wall of a chamber in which the disc is located for creating a vortex air seal barrier between the rotating assembly and the nonforaminous outer wall during turbine operation, without physical contact between the rotating assembly and the housing through the disc means, and effective for blocking escape of drive air from the housing around the rotating assembly during turbine operation.

38. The improvement according to claim 37 wherein said disc means is spaced a distance less than 0.010 inches from said internal surface.

39. The improvement according to claim 38 wherein said internal surface and a surface of said disc means facing said internal surface extend generally parallel with respect to each other.

40. The improvement according to claim 39, wherein said surface of said disc means and said internal surface extend generally perpendicularly from a longitudinal axis of said assembly.

41. The improvement according to claim 40 wherein said assembly is supported by bearings which are mounted for axial movement in a cavity in said housing for bringing said disc means into contact with said internal surface and manually braking rotation of said turbine and said assembly.

42. The improvement according to claim 40 wherein said assembly is supported by bearings which are mounted for axial movement in a cavity in said housing for bringing said surface of said disc means into contact with said internal surface and manually braking rotation of said turbine and said assembly.

43. In a high-speed dental handpiece having a collet and an air-driven turbine mounted within a housing for rotating the collet extending through an aperture in the housing, the improvement comprising a chamber defined by a nonforaminous outer wall formed by a recessed surface surrounding said aperture and a wall extending from the recessed surface, and a disc located in said chamber and mounted to said collet for rotation therewith, the disc being in close proximity to the surface and radially spaced from the wall to form an active air seal between the disc and the nonforaminous outer wall of the chamber during rotation of the collet, the active air seal minimizing turbine air loss and preventing ingress of unwanted material into the turbine during power-off run down of the turbine.

44. A high speed handpiece according to claim 43 wherein the disc is less than about 0.010 inches from the surface.

45. In a high speed dental handpiece having a collet and an air-driven turbine mounted within a housing for rotating the collet extending through an aperture in the housing, the housing including an internal surface surrounding said aperture, the improvement comprising a chamber defined by a nonforaminous outer wall and a disc mounted to rotate with said collet in said chamber, the nonforaminous outer wall comprising the internal surface and a wall extending from said surface, said disc being spaced a predetermined distance from said internal surface, said predetermined distance being selected to provide an active air seal between said disc and internal surface during rotation of the collet, the active air seal minimizing turbine air loss and preventing ingress of unwanted material into the turbine during power-off run down of the turbine.

46. A high speed handpiece according to claim 45 wherein the predetermined distance is less than about 0.010 inches.

47. A high speed dental handpiece according to claim 45 wherein the disc and internal surface extend generally parallel with respect to each other.

48. A high speed dental handpiece according to claim 45 wherein the active air seal is in the form of vortexes formed between the disc and internal surface during rotation of the collet.

49. A high speed dental handpiece as recited in claim 45, wherein the disc and internal surface extend generally perpendicularly from a longitudinal axis of the collet.

50. In a high speed dental handpiece having an assembly and a high speed, air-driven turbine mounted within a housing for rotating the assembly extending through an aperture in the housing at operating speeds of 100,000 RPM or more, the housing including a stationary internal surface surrounding said aperture, the improvement comprising a chamber defined by a nonforaminous outer wall and disc means rotating with the assembly in said chamber, the nonforaminous outer wall including the internal surface and a wall radially spaced from the disc means which extends from the internal surface, the disc means overlapping the internal surface and creating a vortex air seal barrier between the rotating assembly and the nonforaminous outer wall during turbine operation, without physical contact between the rotating assembly and the housing through the disc means, the barrier being effective for blocking escape of drive air from the housing around the rotating assembly during turbine operation.

51. The improvement according to claim 50 wherein the disc means is spaced a distance less than 0.010 inches from the internal surface.

52. The improvement according to claim 51 wherein the internal surface and a surface of the disc means facing the internal surface extend generally parallel with respect to each other.

53. The improvement according to claim 52, wherein the surface of the disc means and the internal surface extend generally perpendicularly from a longitudinal axis of the assembly.

54. The improvement according to claim 53 wherein the assembly is supported by bearings which are mounted for axial movement in a cavity in the housing for bringing the disc means into contact with the internal surface and manually braking rotation of the turbine and the assembly.

55. The improvement according to claim 53 wherein the assembly is supported by bearings which are mounted for axial movement in a cavity in the housing for bringing the surface of the disc means into contact with the internal surface and manually braking rotation of the turbine and the assembly.

\* \* \* \* \*